US010688028B2

(12) United States Patent
Menon et al.

(10) Patent No.: US 10,688,028 B2
(45) Date of Patent: *Jun. 23, 2020

(54) SOLID STICK ANTIPERSPIRANT COMPOSITIONS HAVING NON-VOLATILE SILICONES

(71) Applicant: The Procter & Gamble Company, Cincinnati, OH (US)

(72) Inventors: Elton Luis Menon, Mason, OH (US); David Frederick Swaile, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/868,043

(22) Filed: Jan. 11, 2018

(65) Prior Publication Data
US 2018/0133132 A1 May 17, 2018

Related U.S. Application Data

(63) Continuation of application No. 14/793,121, filed on Jul. 7, 2015, now Pat. No. 9,872,819.

(51) Int. Cl.
A61K 8/26 (2006.01)
A61K 8/34 (2006.01)
A61K 8/37 (2006.01)
A61Q 15/00 (2006.01)
A61K 8/891 (2006.01)
A61K 8/02 (2006.01)
A61K 8/04 (2006.01)
A61K 8/92 (2006.01)

(52) U.S. Cl.
CPC ............ A61K 8/26 (2013.01); A61K 8/0229 (2013.01); A61K 8/044 (2013.01); A61K 8/342 (2013.01); A61K 8/37 (2013.01); A61K 8/891 (2013.01); A61K 8/92 (2013.01); A61Q 15/00 (2013.01); A61K 2800/20 (2013.01); A61K 2800/30 (2013.01); A61K 2800/31 (2013.01)

(58) Field of Classification Search
CPC .... A61K 2800/31; A61K 8/0229; A61K 8/26; A61K 8/342; A61K 8/92; A61K 8/891; A61K 8/04; A61Q 15/00
See application file for complete search history.

(56) References Cited

U.S. PATENT DOCUMENTS

| 3,792,068 | A | 2/1974 | Luedders et al. |
| 3,887,692 | A | 6/1975 | Gilman |
| 3,904,741 | A | 9/1975 | Jones et al. |
| 4,049,792 | A | 9/1977 | Elsnau |
| 4,120,948 | A | 10/1978 | Shelton |
| 4,359,456 | A | 11/1982 | Gosling et al. |
| 5,019,375 | A | 5/1991 | Tanner et al. |
| 5,232,689 | A | 8/1993 | Katsoulis |
| 5,429,816 | A | 7/1995 | Hofrichter et al. |
| 5,840,287 | A | 11/1998 | Guskey et al. |
| 5,891,424 | A | 4/1999 | Bretzler et al. |
| 5,968,489 | A | 10/1999 | Swaile et al. |
| 5,976,514 | A | 11/1999 | Guskey et al. |
| 6,013,248 | A | 1/2000 | Luebbe et al. |
| 6,241,976 | B1 * | 6/2001 | Esser ..................... A61K 8/042 424/400 |
| 8,147,808 | B2 | 4/2012 | Scavone et al. |
| 9,872,819 | B2 * | 1/2018 | Menon ..................... A61K 8/26 |
| 2004/0241200 | A1 | 12/2004 | Winn et al. |
| 2006/0013843 | A1 * | 1/2006 | Shimizu ................... A61K 8/37 424/401 |
| 2007/0003499 | A1 | 1/2007 | Shen et al. |
| 2009/0304617 | A1 * | 12/2009 | Banowski ................ A61K 8/02 424/68 |
| 2012/0121525 | A1 | 5/2012 | Ledingham et al. |
| 2012/0177589 | A1 * | 7/2012 | Banowski ............ A61K 8/0229 424/65 |
| 2014/0037567 | A1 | 2/2014 | Sturgis et al. |
| 2016/0199287 | A1 * | 7/2016 | Banowski ................ A61K 8/26 424/68 |
| 2017/0007515 | A1 | 1/2017 | Menon et al. |

FOREIGN PATENT DOCUMENTS

| BE | 825146 A1 | 8/1975 | |
| GB | 1347950 | 2/1974 | |
| GB | 2048229 A | 12/1980 | |
| GB | 2144992 A | 3/1985 | |
| WO | WO-2010046012 A2 * | 4/2010 | ............... A61K 8/02 |

OTHER PUBLICATIONS

Bashimam (Journal of Chemical and Pharmaceutical Research, 2015, vol. 7, pp. 597-599) (Year: 2015).*
CRC Press (Solubility Parameters—An Introduction, Chapter 1, copyright 2000) (Year: 2000).*
Personal Care Magazine (Selecting the Perfect Silicone for Your Formulation, Jul. 2014, https://www.personalcarennagazine.com/story/13149/selecting-the-perfect-silicone-for-your-formulation) (Year: 2014).*
Miertsch WO 2010/046012, Google English Translation on WIPO site, downloaded in Oct. 2018 (Year: 2018).*
Beiersdorf 8x4 Direct Fit Stick Deodorant, Mintel GNPD Database Record ID: 1329999, Feb. 2010.
Molton Brown Anti-Perspirant Sportstick, Mintel GNPD Database Record ID: 2100999, Jul. 2013.
PCT International Search Report dated Sep. 16, 2016 (20 pages).
Swiftcraftymonkey blog, (C12-15 alkyl benzoate, http://swiftcraftymonkey.blogspo.com/2010/08/esters-c12-15-alkyl-benzoate.html, posted on Aug. 11, 2010).

* cited by examiner

Primary Examiner — Mark V Stevens
(74) Attorney, Agent, or Firm — Kathleen Y. Carter

(57) ABSTRACT

Solid stick antiperspirant compositions include an antiperspirant active, one or more waxes, and a plurality of liquids. The one or more waxes include a polar wax. The plurality of liquids include about 60% or greater, by weight of the plurality of liquids, of a non-volatile silicone. The solid stick antiperspirant composition is substantially or completely free of volatile silicones. Antiperspirant product containing solid stick antiperspirant compositions are also described herein.

16 Claims, 1 Drawing Sheet

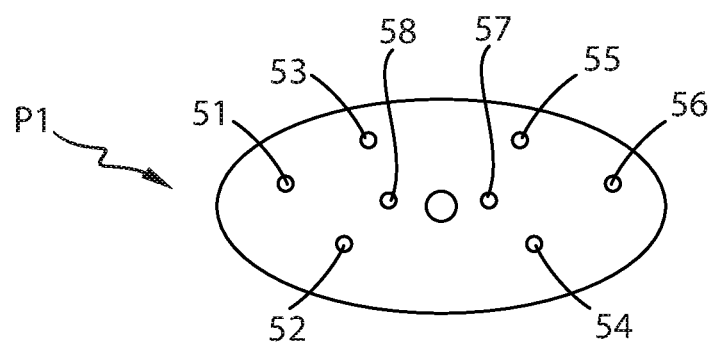

SOLID STICK ANTIPERSPIRANT COMPOSITIONS HAVING NON-VOLATILE SILICONES

CROSS REFERENCE TO RELATED APPLICATION

This application is a continuation of application Ser. No. 14/793,121, filed Jul. 7, 2015, the substance of which is incorporated herein by reference.

TECHNICAL FIELD

The present disclosure generally relates to solid stick antiperspirant compositions having non-volatile silicones.

BACKGROUND

There are many types of antiperspirant products that are commercially available or otherwise known in the art, and there are many factors that can contribute to the purchase intent of a consumer when looking for such products (e.g., odor and wetness protection, residue, and skin feel). When formulating antiperspirant products, a balance can often be struck between performance and other properties which encourage purchase.

Solid stick antiperspirant compositions can typically include antiperspirant actives in a structurant system, which can typically include a mixture of waxes and/or liquids. A plurality of liquids, such as emollients, can be used in the solid stick antiperspirant compositions to facilitate gliding and dispensing of the product onto skin. Further, the plurality of liquids can be used to improve processability and dispersion of solid particles in the product. Accordingly, the plurality of liquids in a solid stick antiperspirant composition can be important in achieving a balance in such desirable properties as described above. One of such liquids is decamethylcyclopentasiloxane ($D_5$). However, due to its long half-life in the environment, $D_5$ has come under regulatory scrutiny, and options for its replacement are being sought. Therefore, what is desired is a solid stick antiperspirant composition including having a non-volatile silicone, where the antiperspirant composition can provide odor protection, a consumer-preferred "feel," improved processability, and compatibility with a structurant system, while minimizing skin irritation and clothing stains, satisfying regulatory standards, and remaining a cost effective option.

SUMMARY

In accordance with one example, a solid stick antiperspirant composition includes an antiperspirant active, one or more waxes, and a plurality of liquids. The one or more waxes include a polar wax. The plurality of liquids include two or more emollients. A first emollient of the two or more emollients includes a non-volatile silicone. The plurality of liquids include about 60% or greater, by weight, of the non-volatile silicone. The plurality of liquids have an aggregate polarity from about 0.9 $MPa^{1/2}$ to about 3.4 $MPa^{1/2}$. The solid stick antiperspirant composition is substantially or completely free of volatile silicone fluids.

In accordance with another example, a solid stick antiperspirant composition includes an antiperspirant active, one or more waxes, and a plurality of liquids. The one or more waxes include a polar wax. The plurality of liquids include about 60% or greater, by weight, of a polydimethylsiloxane. The polydimethylsiloxane has a viscosity of about 10 centistokes or less. The plurality of liquids further include about 10% or greater, by weight, of one or more co-emollients. The one or more co-emollients have an aggregate polarity from about 3.5 $MPa^{1/2}$ to about 5.5 $MPa^{1/2}$. The solid stick antiperspirant composition is substantially or completely free of volatile silicone fluids.

In accordance with yet another example, an antiperspirant product includes a package having an interior chamber and a solid stick antiperspirant composition stored in the interior chamber. The solid stick antiperspirant composition includes an antiperspirant active, one or more waxes, and a plurality of liquids. The one or more waxes include a polar wax. The plurality of liquids include about 60% or greater, by weight, of a polydimethylsiloxane. The polydimethylsiloxane has a viscosity of about 10 centistokes or less. The plurality of liquids further include about 10% or greater, by weight, of one or more co-emollients. The solid stick antiperspirant composition is substantially or completely free of volatile silicones. The one or more waxes and the plurality of liquids, when mixed, exhibit a cloud point temperature between about 45° C. and about 65° C.

In accordance with still another example, a solid stick antiperspirant composition includes an antiperspirant active, one or more waxes, and a plurality of liquids. The one or more waxes include from about 12% to about 20%, by weight of the solid stick antiperspirant composition, of stearyl alcohol. The plurality of liquids include about 30% or greater, by weight of the solid stick antiperspirant composition, of a polydimethylsiloxane. The polydimethylsiloxane has a viscosity of about 10 centistokes or less. The plurality of liquids further include one or more co-emollients. The one or more co-emollients are selected from the group consisting of $C_{12\text{-}15}$ alkyl benzoate, isopropyl myristate, isopropyl palmitate, and octyldodecanol. The solid stick antiperspirant composition is substantially or completely free of volatile silicones. The solid stick antiperspirant composition exhibits an average standard deviation of about 5 or less for penetration peak force measurements taken in accordance with the Penetration Test Method as described herein.

BRIEF DESCRIPTION OF THE DRAWINGS

FIG. 1 depicts a schematic view of an exemplary test location pattern for use with the Penetration Test Method as described herein.

DETAILED DESCRIPTION

I. Definitions

As used herein, the following terms shall have the meaning specified thereafter:

"Aggregate polarity" as used herein is defined by the Hansen Solubility Parameter for polarity described herein.

"Anhydrous" as used herein refers to being substantially or completely free of free or added water. From a formulation standpoint, anhydrous solid stick antiperspirant compositions can include about 2% or less, about 1% or less, about 0.1% or less, or more specifically, zero percent, by weight of free or added water, other than the water of hydration typically associated with the particulate antiperspirant active prior to formulation.

"Ambient conditions" as used herein refers to surrounding conditions under about one atmosphere of pressure, at about 50% relative humidity, and at about 25° C., unless otherwise specified. All values, amounts, and measurements described herein are obtained under ambient conditions unless otherwise specified.

"Solid structurant" as used herein refers to any material known or otherwise effective in providing suspending, gelling, viscosifying, solidifying, and/or thickening properties to a solid stick antiperspirant composition or which can otherwise provide structure to a final product form.

"Substantially free of" refers to about 2% or less, about 1% or less, or about 0.1% or less of a stated ingredient. "Free of" refers to no detectable amount of the stated ingredient or thing.

"Volatile" as used herein refers to those materials that have a measurable vapor pressure at 25° C. Such vapor pressures can typically range from about 0.01 millimeters of mercury (mm Hg) to about 6 mmHg, and more typically, from about 0.02 mmHg to about 1.5 mmHg. Further, such vapor pressures can typically have an average boiling point at one (1) atmosphere of pressure of less than about 250° C., and more typically, less than about 235° C. Conversely, the term "non-volatile" refers to those materials that are not "volatile" as defined herein.

II. Solid Stick Antiperspirant Compositions

Decamethylcyclopentasiloxane ($D_5$) is known to be a widely-used ingredient in beauty and personal care applications, but in view of mounting regulatory and safety pressures, options for replacing $D_5$ are being sought. Because of the unique physical and chemical properties of $D_5$, there are no readily available replacements that can provide a safe and chemically-compatible viable alternative. Polydimethylsiloxane, for example, bears some similarity to $D_5$ with respect to cosmetic attributes, but on its own, polydimethylsiloxane does not possess a polarity that can sufficiently melt waxes and provide for adequate processability of a solid stick antiperspirant composition. However, it has been determined that polydimethylsiloxane can be combined with a co-emollient to provide an adequate replacement for $D_5$, such that a resulting combination of polydimethylsiloxane and the other emollient can provide the desired processability, product stability, and compatibility with a structurant system for a solid stick antiperspirant composition, while minimizing skin irritation and clothing stains, satisfying regulatory standards, and remaining a cost effective option.

In determining which liquids (e.g., emollients) can be combined with polydimethylsiloxane to achieve desired product characteristics as described above, processing conditions can be taken into consideration. A desired combination of emollients can dissolve one or more waxes into a homogeneous solution once heated. Likewise, the emollient combination can allow the one or more waxes to come out of solution upon cooling, such that the solid stick antiperspirant composition can quickly solidify upon being poured into and stored in an interior chamber of a package, for example. This can promote homogeneity in the solid stick antiperspirant composition; such that the solid stick antiperspirant composition can be dispensed consistently during the life of the product. In particular, quick solidification of waxes can prevent active particles from settling within the product.

The Cloud Point Test, which is described below in greater detail, can be used to determine a desired polydimethylsiloxane. For example, a polydimethylsiloxane formulation having a 50-centistoke viscosity could not dissolve waxes at 85° C. Similarly, waxes began to come out of a liquid phase (e.g., solidify) in a 10-centistoke polydimethylsiloxane formulation at 75° C. In certain examples, it can be desirable for a composition of emollients and waxes to lose solubility at about 60° C. and begin to solidify at about 55° C. Therefore, in such examples, a polydimethylsiloxane formulation having a lower viscosity (e.g., 5 centistokes) can provide a more acceptable option with respect to processability.

The Penetration Test Method, which is also described below, can be used to verify the improved product uniformity predicted by the Cloud Point Test. The Penetration Test Method can be one technique for measuring product uniformity, particularly for solid stick antiperspirant compositions. For example, Table 1 shows that a formulation including polydimethylsiloxane having a viscosity of 5 centistokes exhibited the lowest standard deviation for force across the surface of a solid stick antiperspirant composition, when compared with a formulation including polydimethylsiloxane having a viscosity of 10 centistokes and another with a viscosity of 50 centistokes. If a solid stick antiperspirant composition lacks homogeneity, liquids can weep from the solid stick antiperspirant composition, giving rise to syneresis. Furthermore, in a solid stick, which is a self-dosing product, lack of homogeneity compromises the ability of the product to deliver uniform doses through its life. Thus, homogeneity of an antiperspirant composition can provide improved product stability and guarantee reproducible dosing of the product.

TABLE 1

Maximum Force Measured Across Surface of a Solid Stick Antiperspirant Composition (Test Examples 1-3)

| | Force (g) | | |
| --- | --- | --- | --- |
| Readings | Test Example 1 (5-cst Formulation) | Test Example 2 (10-cst Formulation) | Test Example 3 (50-cst Formulation) |
| 1 | 104.5 | 92 | 114.2 |
| 2 | 106.3 | 95.1 | 113.9 |
| 3 | 102.1 | 75.8 | 85.9 |
| 4 | 104.3 | 97.9 | 108.3 |
| 5 | 105.2 | 104 | 116.2 |
| 6 | 99.8 | 94.5 | 109.3 |
| 7 | 99.5 | 78.6 | 83 |
| 8 | 105.3 | 86.1 | 91.3 |
| AVERAGE | 103.4 | 90.5 | 102.8 |
| STDEV | 2.6 | 9.7 | 13.7 |
| % STDEV | 2.5 | 10.7 | 13.3 |

The Cloud Point Test can also be used to determine which emollients can be combined with polydimethylsiloxane to properly hold molten the waxes during formation of the solid stick antiperspirant composition. While emollients can provide a desired polarity and other processing properties, it can also be desirable to limit the amount of emollients used in the solid stick antiperspirant composition. For example, overuse of emollients can result in skin irritation and/or clothing stains. Furthermore, large amounts of emollients can increase polarity such that compatibility between the emollients and the waxes can be negatively affected. Additionally, polar non-volatile emollients can tend to suppress fragrance expression in a solid antiperspirant product. Thus, it can be desirable to minimize the amount of emollients used in antiperspirant composition to achieve a desired product.

Tables 2-6 below illustrate cloud point temperatures for several test example compositions in order to determine which emollient combinations can provide desired processability properties and in what amount these emollient combinations can be included to do so. In certain examples, emollients and waxes, when mixed in the same proportions as in the solid stick antiperspirant composition, can exhibit a cloud point temperature between 45° C. and 65° C. For example, in Table 2, none of the test example compositions provide a desired cloud point temperature; all of the cloud point temperatures are above 80° C. After increasing the respective amounts of emollients, as shown in Tables 3-6, some of the test example compositions can provide a cloud point temperature within a desired range.

TABLE 2

Cloud Point Temperatures for Test Example Compositions 4-14

| | Amount (wt. %) | | | | | | | | | | |
|---|---|---|---|---|---|---|---|---|---|---|---|
| Ingredient | Test Ex. 4 | Test Ex. 5 | Test Ex. 6 | Test Ex. 7 | Test Ex. 8 | Test Ex. 9 | Test Ex. 10 | Test Ex. 11 | Test Ex. 12 | Test Ex. 13 | Test Ex. 14 |
| Isopropyl Myristate | 8.23 | — | — | — | — | — | — | — | — | — | — |
| Mineral Oil | — | 8.23 | — | — | — | — | — | — | — | — | — |
| Octyldodecanol | — | — | 8.23 | — | — | — | — | — | — | — | — |
| FINSOLV ™ | — | — | — | 8.23 | — | — | — | — | — | — | — |
| $D_5$ | — | — | — | — | 8.23 | — | — | — | — | — | — |
| PPG-14 Butyl Ether | — | — | — | — | — | 8.23 | — | — | — | — | — |
| Dipropylene Glycol | — | — | — | — | — | — | 8.23 | — | — | — | — |
| Isopropyl Palmitate | — | — | — | — | — | — | — | 8.23 | — | — | — |
| Isohexadecane | — | — | — | — | — | — | — | — | 8.23 | — | — |
| Butyl Stearate | — | — | — | — | — | — | — | — | — | 8.23 | — |
| di-(2-propyl-heptyl-) carbonate | — | — | — | — | — | — | — | — | — | — | 8.23 |
| Polydimethyl-siloxane (5 cst) | 57.62 | 57.62 | 57.62 | 57.62 | 57.62 | 57.62 | 57.62 | 57.62 | 57.62 | 57.62 | 57.62 |
| Stearyl Alcohol | 26.34 | 26.34 | 26.34 | 26.34 | 26.34 | 26.34 | 26.34 | 26.34 | 26.34 | 26.34 | 26.34 |
| Hydrogenated Castor Oil | 7.81 | 7.81 | 7.81 | 7.81 | 7.81 | 7.81 | 7.81 | 7.81 | 7.81 | 7.81 | 7.81 |
| Cloud Point Temperature (° C.) | 80 | >85 | >85 | >85 | >85 | >85 | >85 | 80.7 | >85 | 81 | 81 |

TABLE 3

Cloud Point Temperatures for Test Example Compositions 15-25

| | Amount (wt. %) | | | | | | | | | | |
|---|---|---|---|---|---|---|---|---|---|---|---|
| Ingredient | Test Ex. 15 | Test Ex. 16 | Test Ex. 17 | Test Ex. 18 | Test Ex. 19 | Test Ex. 20 | Test Ex. 21 | Test Ex. 22 | Test Ex. 23 | Test Ex. 24 | Test Ex. 25 |
| Isopropyl Myristate | 16.46 | — | — | — | — | — | — | — | — | — | — |
| Mineral Oil | — | 16.46 | — | — | — | — | — | — | — | — | — |
| Octyldodecanol | — | — | 16.46 | — | — | — | — | — | — | — | — |
| FINSOLV ™ | — | — | — | 16.46 | — | — | — | — | — | — | — |
| $D_5$ | — | — | — | — | 16.46 | — | — | — | — | — | — |
| PPG-14 Butyl Ether | — | — | — | — | — | 16.46 | — | — | — | — | — |
| Dipropylene Glycol | — | — | — | — | — | — | 16.46 | — | — | — | — |
| Isopropyl Palmitate | — | — | — | — | — | — | — | 16.46 | — | — | — |
| Isohexadecane | — | — | — | — | — | — | — | — | 16.46 | — | — |
| Butyl Stearate | — | — | — | — | — | — | — | — | — | 16.46 | — |
| di-(2-propyl-heptyl-) carbonate | — | — | — | — | — | — | — | — | — | — | 16.46 |
| Polydimethyl-siloxane (5 cst) | 49.39 | 49.39 | 49.39 | 49.39 | 49.39 | 49.39 | 49.39 | 49.39 | 49.39 | 49.39 | 49.39 |
| Stearyl Alcohol | 26.34 | 26.34 | 26.34 | 26.34 | 26.34 | 26.34 | 26.34 | 26.34 | 26.34 | 26.34 | 26.34 |
| Hydrogenated Castor Oil | 7.81 | 7.81 | 7.81 | 7.81 | 7.81 | 7.81 | 7.81 | 7.81 | 7.81 | 7.81 | 7.81 |
| Cloud Point Temperature (° C.) | 57 | 69 | 75 | 71 | >85 | >85 | >85 | 58 | 65 | 59 | 65 |

TABLE 4

Cloud Point Temperatures for Test Example Compositions 26-36

| Ingredient | Amount (wt. %) | | | | | | | | | | |
|---|---|---|---|---|---|---|---|---|---|---|---|
| | Test Ex. 26 | Test Ex. 27 | Test Ex. 28 | Test Ex. 29 | Test Ex. 30 | Test Ex. 31 | Test Ex. 32 | Test Ex. 33 | Test Ex. 34 | Test Ex. 35 | Test Ex. 36 |
| Isopropyl Myristate | 19.76 | — | — | — | — | — | — | — | — | — | — |
| Mineral Oil | — | 19.76 | — | — | — | — | — | — | — | — | — |
| Octyldodecanol | — | — | 19.76 | — | — | — | — | — | — | — | — |
| FINSOLV ™ | — | — | — | 19.76 | — | — | — | — | — | — | — |
| $D_5$ | — | — | — | — | 19.76 | — | — | — | — | — | — |
| PPG-14 Butyl Ether | — | — | — | — | — | 19.76 | — | — | — | — | — |
| Dipropylene Glycol | — | — | — | — | — | — | 19.76 | — | — | — | — |
| Isopropyl Palmitate | — | — | — | — | — | — | — | 19.76 | — | — | — |
| Isohexadecane | — | — | — | — | — | — | — | — | 19.76 | — | — |
| Butyl Stearate | — | — | — | — | — | — | — | — | — | 19.76 | — |
| di-(2-propyl-heptyl-) carbonate | — | — | — | — | — | — | — | — | — | — | 19.76 |
| Polydimethyl-siloxane (5 cst) | 46.09 | 46.09 | 46.09 | 46.09 | 46.09 | 46.09 | 46.09 | 46.09 | 46.09 | 46.09 | 46.09 |
| Stearyl Alcohol | 26.34 | 26.34 | 26.34 | 26.34 | 26.34 | 26.34 | 26.34 | 26.34 | 26.34 | 26.34 | 26.34 |
| Hydrogenated Castor Oil | 7.81 | 7.81 | 7.81 | 7.81 | 7.81 | 7.81 | 7.81 | 7.81 | 7.81 | 7.81 | 7.81 |
| Cloud Point Temperature (° C.) | 55 | 65 | 68 | 64 | >85 | >85 | >85 | 55 | 62 | 57 | 57 |

TABLE 5

Cloud Point Temperatures for Test Example Compositions 37-47

| Ingredient | Amount (wt. %) | | | | | | | | | | |
|---|---|---|---|---|---|---|---|---|---|---|---|
| | Test Ex. 37 | Test Ex. 38 | Test Ex. 39 | Test Ex. 40 | Test Ex. 41 | Test Ex. 42 | Test Ex. 43 | Test Ex. 44 | Test Ex. 45 | Test Ex. 46 | Test Ex. 47 |
| Isopropyl Myristate | 26.34 | — | — | — | — | — | — | — | — | — | — |
| Mineral Oil | — | 26.34 | — | — | — | — | — | — | — | — | — |
| Octyldodecanol | — | — | 26.34 | — | — | — | — | — | — | — | — |
| FINSOLV ™ | — | — | — | 26.34 | — | — | — | — | — | — | — |
| $D_5$ | — | — | — | — | 26.34 | — | — | — | — | — | — |
| PPG-14 Butyl Ether | — | — | — | — | — | 26.34 | — | — | — | — | — |
| Dipropylene Glycol | — | — | — | — | — | — | 26.34 | — | — | — | — |
| Isopropyl Palmitate | — | — | — | — | — | — | — | 26.34 | — | — | — |
| Isohexadecane | — | — | — | — | — | — | — | — | 26.34 | — | — |
| Butyl Stearate | — | — | — | — | — | — | — | — | — | 26.34 | — |
| di-(2-propyl-heptyl-) carbonate | — | — | — | — | — | — | — | — | — | — | 26.34 |
| Polydimethyl-siloxane (5 cst) | 39.51 | 39.51 | 39.51 | 39.51 | 39.51 | 39.51 | 39.51 | 39.51 | 39.51 | 39.51 | 39.51 |
| Stearyl Alcohol | 26.34 | 26.34 | 26.34 | 26.34 | 26.34 | 26.34 | 26.34 | 26.34 | 26.34 | 26.34 | 26.34 |
| Hydrogenated Castor Oil | 7.81 | 7.81 | 7.81 | 7.81 | 7.81 | 7.81 | 7.81 | 7.81 | 7.81 | 7.81 | 7.81 |
| Cloud Point Temperature (° C.) | 53 | 60 | 61 | 56 | >85 | >85 | >85 | 54 | 58 | 53 | 53 |

TABLE 6

Cloud Point Temperatures for Test Example Compositions 48-58

| Ingredient | Amount (wt. %) | | | | | | | | | | |
|---|---|---|---|---|---|---|---|---|---|---|---|
| | Test Ex. 48 | Test Ex. 49 | Test Ex. 50 | Test Ex. 51 | Test Ex. 52 | Test Ex. 53 | Test Ex. 54 | Test Ex. 55 | Test Ex. 56 | Test Ex. 57 | Test Ex. 58 |
| Isopropyl Myristate | 32.92 | — | — | — | — | — | — | — | — | — | — |
| Mineral Oil | — | 32.92 | — | — | — | — | — | — | — | — | — |
| Octyldodecanol | — | — | 32.92 | — | — | — | — | — | — | — | — |
| FINSOLV ™ | — | — | — | 32.92 | — | — | — | — | — | — | — |
| $D_5$ | — | — | — | — | 32.92 | — | — | — | — | — | — |
| PPG-14 Butyl Ether | — | — | — | — | — | 32.92 | — | — | — | — | — |
| Dipropylene Glycol | — | — | — | — | — | — | 32.92 | — | — | — | — |
| Isopropyl Palmitate | — | — | — | — | — | — | — | 32.92 | — | — | — |
| Isohexadecane | — | — | — | — | — | — | — | — | 32.92 | — | — |
| Butyl Stearate | — | — | — | — | — | — | — | — | — | 32.92 | — |
| di-(2-propyl-heptyl-)carbonate | — | — | — | — | — | — | — | — | — | — | 32.92 |
| Polydimethyl-siloxane (5 cst) | 32.93 | 32.93 | 32.93 | 32.93 | 32.93 | 32.93 | 32.93 | 32.93 | 32.93 | 32.93 | 32.93 |
| Stearyl Alcohol | 26.34 | 26.34 | 26.34 | 26.34 | 26.34 | 26.34 | 26.34 | 26.34 | 26.34 | 26.34 | 26.34 |
| Hydrogenated Castor Oil | 7.81 | 7.81 | 7.81 | 7.81 | 7.81 | 7.81 | 7.81 | 7.81 | 7.81 | 7.81 | 7.81 |
| Cloud Point Temperature (° C.) | 51 | 58 | 51 | 50 | 67 | >85 | >85 | 51 | 54 | 50 | 52 |

Based on the results shown in Tables 2-6, it was observed that a minimum ratio of emollients to a total amount of liquids was required to have a cloud point temperature within a desired range. Accordingly, it was discovered that the minimum ratio of emollients to a total amount of liquids corresponded to aggregate polarity range. As defined herein, the aggregate polarity can be calculated using the Hansen Solubility Parameter (HSP) for Polarity and the following equation:

Aggregate Polarity=ΣLiquid Ratio×Liquid HSP for Polarity wherein the Liquid Ratio is a weight percent of a liquid, by weight of the total concentration of liquids.

Table 7 shows aggregate polarity values for each of the Test Example Compositions 4-58 from Tables 2-6. In certain examples, one or more liquids have an aggregate polarity from about 0.9 MPa$^{1/2}$ to about 3.4 MPa$^{1/2}$. By using liquid combinations with an aggregate polarity in a desired range, solid stick antiperspirant compositions can be formed having desired processability properties.

TABLE 7

Aggregate Polarity for Test Example Compositions 4-58

| Ingredient | Aggregate Polarity (MPa$^{1/2}$) | | | | |
|---|---|---|---|---|---|
| | Test Ex. 4-14 | Test Ex. 15-25 | Test Ex. 26-36 | Test Ex. 37-47 | Test Ex. 48-58 |
| Isopropyl Myristate | 1.2 | 1.8 | 2.0 | 2.4 | 2.9 |
| Mineral Oil | 0.8 | 0.9 | 1.0 | 1.1 | 1.2 |
| Octyldodecanol | 1.0 | 1.4 | 1.5 | 1.7 | 2.0 |
| FINSOLV ™ | 1.1 | 1.5 | 1.7 | 2.1 | 2.4 |
| $D_5$ | 0.7 | 0.7 | 0.7 | 0.7 | 0.7 |
| PPG-14 Butyl Ether | 1.8 | 3.0 | 3.4 | 4.3 | 5.2 |
| Dipropylene Glycol | 1.9 | 3.2 | 3.7 | 4.7 | 5.6 |
| Isoproryl Palmitate | 1.2 | 1.8 | 2.0 | 2.4 | 2.8 |
| Isohexadecane | 0.8 | 0.9 | 0.9 | 1.0 | 1.1 |
| Butyl Stearate | 1.2 | 1.7 | 2.0 | 2.4 | 2.8 |
| di-(2-propyl-heptyl-)carbonate | 1.0 | 1.3 | 1.5 | 1.7 | 2.0 |

Based on cloud point temperatures and aggregate polarity ratios, various liquid compositions having certain emollients can fall within desired ranges, and thus, appear to satisfy certain requirements; however, compatibility with waxes can be another critical factor in determining which co-emollients can be used with polydimethylsiloxane in a solid stick antiperspirant composition. For example, certain waxes or structurants can provide for better distribution than others, while some waxes can be more cost effective. In certain examples, the solid stick antiperspirant composition can include polar waxes, which can include fatty alcohol waxes such as stearyl alcohol. Accordingly, it can be desired that a liquid combination can be compatible with, for example, stearyl alcohol in a solid stick antiperspirant composition. One skilled in the art will appreciate that other suitable polar waxes may be used in the solid stick antiperspirant composition.

A. Liquids

A solid stick antiperspirant composition can include a plurality of liquids at concentrations ranging from about 20% to about 80% or from about 30% to about 70%, by weight of the solid stick antiperspirant composition. Such concentrations can vary depending upon variables such as product form, desired product hardness, and selection of other ingredients in the solid stick antiperspirant composition. Suitable liquids can include those known for use in personal care applications or otherwise suitable for topical application to the skin. Certain liquid components can include emollients.

In certain examples, solid stick antiperspirant compositions can include a non-volatile fluid, and such non-volatile fluids can include either non-volatile silicones or non-volatile organic fluids.

A suitable non-volatile silicone can be a liquid at or below human skin temperature, or otherwise in liquid form within solid stick antiperspirant compositions during or shortly after topical application. The plurality of liquids can include about 60% or greater, by weight of a total concentration of the plurality of liquids, of a non-volatile silicone. Non-volatile silicones can include those which conform to the general formula:

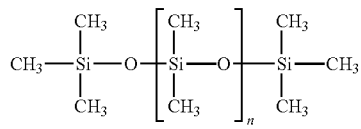

wherein n can be greater than or equal to 4.

Specific non-limiting examples of suitable non-volatile silicones can include Dow Corning 200, Dow Corning 225, Dow Corning 1732, Dow Corning 5732, Dow Corning 5750 (available from Dow Corning Corp.); and SF-96, SF-1066, and SF18(350) Silicone Fluids (available from G.E. Silicones).

Low surface tension non-volatile silicones can also be used. For example, non-volatile silicones can include polydimethylsiloxanes, sometimes referred to as dimethicone. In certain examples, polydimethylsiloxanes can have a viscosity of about 10 centistokes or less; in certain examples from about 2 centistokes to about 6 centistokes; and in certain examples about 5 centistokes. In certain examples, polydimethylsiloxanes can have an average molecular weight from about 800 to about 1200. Polydimethylsiloxanes can have a concentration of about 30% or greater, or from about 25% to about 50%, by weight of the solid stick antiperspirant composition. Polydimethylsiloxanes can have the following general formula:

$$M-D_x-M,$$

wherein M can be $(CH_3)_3SiO$; D can be $((CH_3)_2SiO)$; and x can be from about 4 to about 11.

Other non-limiting examples of suitable non-volatile silicones include dimethicone copolyols, phenyl trimethicones, alkyl dimethicones, alkyl methicones, and mixtures thereof. Other low surface tension non-volatile solvents are also described in U.S. Pat. No. 6,835,373 to Kolodzik et al.

Liquids for a desired antiperspirant composition can include other emollients in addition to a non-volatile silicone, such as polydimethylsiloxane. These additional emollients can have a concentration of about 20% or less, or about 15% or less, by weight of the solid stick antiperspirant composition. In certain examples, the additional emollients can have a concentration of about 10% or greater, or from about 16% to about 40%, by weight of the total concentration of the plurality of liquids. In certain examples, these co-emollients can have an aggregate polarity from about 3.5 $MPa^{1/2}$ to about 5.5 $MPa^{1/2}$.

Non-limiting examples of such co-emollients can include, but are not limited to, mineral oil, PPG-14 butyl ether, isopropyl myristate, isopropyl palmitate, petrolatum, butyl stearate, cetyl octanoate, butyl myristate, myristyl myristate, $C_{12-15}$ alkyl benzoate (e.g., Finsolv™), dipropylene glycol dibenzoate, PPG-15 stearyl ether benzoate and blends thereof (e.g., Finsolv TPP), neopentyl glycol diheptanoate (e.g., Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Other examples of co-emollients are disclosed in U.S. Pat. No. 6,013,248 to Luebbe et al., U.S. Pat. No. 5,968,489 to Swaile et al., U.S. Pat. No. 8,147,808 to Scavone et al., and U.S. Pat. Publication No. 2014/0037567 to Sturgis et al.

A solid stick antiperspirant composition can be substantially or completely free of volatile silicones. A volatile silicone can be a cyclic silicone having from about 3 silicone atoms or more or about 5 silicone atoms or more to about 7 silicone atoms or less or about 6 silicone atoms or less. Examples of such volatile silicones can include, but are not limited to, decamethylcyclopentasiloxane ($D_5$ or cyclomethicone) (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Antiperspirant Active

Solid stick antiperspirant compositions can include an antiperspirant active suitable for application to human skin. The concentration of antiperspirant active in the solid stick antiperspirant composition can be sufficient to provide the desired perspiration wetness and odor control from the solid stick antiperspirant composition formulation selected. Such suitable antiperspirant actives can be in particulate form.

A solid stick antiperspirant composition can include an antiperspirant active at concentrations of from about 0.5% to about 60% by weight of the solid stick antiperspirant composition in certain examples; and in certain examples from about 5% to about 35%, by weight of the solid stick antiperspirant composition. These weight percentages can be calculated on an anhydrous metal salt basis exclusive of water and any complexing agents such as, for example, glycine, and glycine salts. An antiperspirant active as formulated in a solid stick antiperspirant composition can be in the form of dispersed particulate solids having an average particle size or equivalent diameter of about 100 microns or less in certain examples; in certain examples at about 20 microns or less; and in certain examples at about 10 microns or less. In certain examples, a total particulate concentration can be about 30% or less, by weight of the solid stick antiperspirant composition.

An antiperspirant active for use in solid stick antiperspirant compositions can include any compound, composition or other material having antiperspirant activity. The antiperspirant actives can include astringent metallic salts, and especially inorganic and organic salts of aluminum, zirconium and zinc, as well as mixtures thereof. The antiperspirant actives can also include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof. In certain examples, the solid stick antiperspirant composition can be substantially anhydrous.

Aluminum salts for use in the solid stick antiperspirant compositions can include those that conform to the formula:

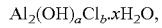

wherein a can be from about 2 to about 5; the sum of a and b can be about 6; x can be from about 1 to about 6; and a, b, and x can have non-integer values.

Specifically, aluminum chlorohydroxides referred to as "⅚ basic chlorohydroxide" can be used, wherein a=5, and "⅔ basic chlorohydroxide", wherein a=4.

Processes for preparing aluminum salts are disclosed in U.S. Pat. No. 3,887,692 to Gilman, issued Jun. 3, 1975; U.S. Pat. No. 3,904,741 to Jones et al., issued Sep. 9, 1975; U.S. Pat. No. 4,359,456 to Gosling et al., issued Nov. 16, 1982; and British Patent Specification 2,048,229 to Fitzgerald et al., published Dec. 10, 1980. These disclosures are incorporated herein by reference for the purpose of describing processes for preparing aluminum salts. Mixtures of aluminum salts are described in British Patent Specification 1,347,950 to Shin et al., published Feb. 27, 1974.

Zirconium salts for use in the solid stick antiperspirant compositions can include those which conform to the formula:

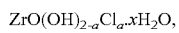

wherein a can be from about 1.5 to about 1.87; x can be from about 1 to about 7; and a and x can both have non-integer values.

These zirconium salts are described in Belgian Patent 825,146 to Schmitz, issued Aug. 4, 1975. Zirconium salts that can additionally include aluminum and glycine, commonly known as "ZAG complexes," can be especially beneficial. Such ZAG complexes can include aluminum chlorohydroxide and zirconyl hydroxy chloride conforming to the above-described formulas. Such ZAG complexes are described in U.S. Pat. No. 3,792,068 to Luedders et al., issued Feb. 12, 1974; Great Britain Patent Application 2,144,992 to Callaghan et al., published Mar. 20, 1985; and U.S. Pat. No. 4,120,948 to Shelton, issued Oct. 17, 1978, disclosures of which can be incorporated herein by reference for the limited purpose of describing ZAG complexes.

Also suitable for use herein can be enhanced efficacy aluminum-zirconium chlorohydrex-amino acid, which typically has the empirical formula $Al_nZr(OH)_{[3n+4-m(n+1)]}(Cl)_{[m(n+1)]}-AA_q$, where n can be from 2.0 to about 10.0, or from about 3.0 to about 8.0; m can be from about 0.48 to about 1.11 (which corresponds to M:Cl approximately equal to 2.1-0.9), or from about 0.56 to about 0.83 (which corresponds to M:Cl approximately equal to 1.8-1.2); q can be from about 0.8 to about 4.0, or from about 1.0 to 2.0; and AA can be an amino acid such as glycine, alanine, valine, serine, leucine, isoleucine, β-alanine, cysteine, β-amino-n-butyric acid, or γ-amino-n-butyric acid, preferably glycine. These salts can also generally have some water of hydration associated with them, typically on the order of 1 to 5 moles per mole of salt (from about 1% to about 16%, or from about 4% to about 13%, by weight). These salts can be generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. Aluminum-zirconium salt can include aluminum-zirconium chlorohydrex-glycine. Additional examples of suitable high efficacy antiperspirant actives can include aluminum zirconium pentachlorohydrex glycine, aluminum zirconium octachlorohydrex glycine, or a combination thereof. These high efficacy actives are more fully described in U.S. App. Pub. No. 2007/0003499 to Shen et al. filed Jun. 30, 2005.

C. Structurants

Solid stick antiperspirant compositions can include a suitable concentration of a primary structurant to help provide the solid stick antiperspirant compositions with a desired viscosity, rheology, texture and/or product hardness, or to otherwise help suspend any dispersed solids or liquids within the solid stick antiperspirant composition.

Solid structurants can include gelling agents, polymeric or non-polymeric agents, inorganic thickening agents, or viscosifying agents. Such materials can typically be solids under ambient conditions and can include organic solids, crystalline or other gellants, inorganic particulates such as clays or silicas, or combinations thereof.

A concentration and type of solid structurant selected for use in solid stick antiperspirant compositions can vary depending upon desired product hardness, rheology, and/or other related product characteristics. A total structurant concentration, for one or more waxes, for example, can range from about 5% to about 35% or from about 15% to about 25%, by weight of the solid stick antiperspirant composition.

Non-limiting examples of suitable gelling agents can include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, polar waxes (e.g., fatty alcohol waxes, ethoxylated fatty alcohol waxes, hydrogenated castor oil, solid triglycerides, and natural waxes), sucrose esters such as SEFA behenate, inorganic materials such as clays or silicas, other amide or polyamide gellants, and mixtures thereof.

Suitable gelling agents can include fatty acid gellants such as fatty acid and hydroxyl or alpha hydroxyl fatty acids, having a carbon chain length from about 10 to about 40, and esters and amides of such gelling agents. Non-limiting examples of such gelling agents can include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents can include 12-hydroxystearic acid, esters of 12-hydroxystearic acid, amides of 12-hydroxystearic acid, and combinations thereof.

Other suitable gelling agents can include amide gellants such as disubstituted or branched monoamide gellants, monsubstituted or branched diamide gellants, triamide gellants, and combinations thereof, including n-acyl amino acid derivatives, such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

As described above, suitable gelling agents can include polar waxes. Polar waxes can be advantageous over non-polar waxes, as non-polar waxes can be less favorable for wetting powders on compositions. Polar waxes can include fatty alcohol waxes having a carbon chain length from about 12 to about 40, or from about 14 to about 24. For example, fatty alcohol waxes can include, but are not limited to behenyl alcohol, ceryl alcohol, ceteryl alcohol, cetyl alcohol, myristyl alcohol, stearyl alcohol and combinations thereof. The polar waxes can have a concentration from about 5% to about 35%, from about 10% to about 20%, or from about 12% to about 20%, by weight of the solid stick antiperspirant composition.

Non-limiting examples of suitable tryiglyceride gellants can include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C(Syncrowax® available from Croda, Inc.).

Suitable structurants can include waxes or wax-like materials having a melt point of 65° C. or higher or from about 65° C. to about 130° C., examples of which can include, but are not limited to, waxes such as beeswax, carnauba, bayberry, candelilla, montan, ozokerite, ceresin, hydrogenated castor oil (castor wax), synthetic waxes (e.g., Fisher-Tropsch waxes), and microcrystalline waxes. Other high melting point waxes are described in U.S. Pat. No. 4,049,792 to Elsnau, issued Sep. 20, 1977.

Further thickening agents for use in solid stick antiperspirant compositions can include inorganic particulate thickening agents such as clays and colloidal pyrogenic silica pigments. For example, colloidal pyrogenic silica pigments such as Cab-O-Sil®, a submicroscopic particulated pyrogenic silica can be used. Other known or otherwise effective inorganic particulate structurants commonly used in the art can also be used in solid stick antiperspirant compositions. Concentrations of particulate structurants can range, for example, from about 0.1% or greater, about 1% or greater, about 5% or greater to about 35% or less, about 15% or less, about 10% or less, or about 8% or less, by weight of the solid stick antiperspirant composition.

Suitable clay structurants can include montmorillonite clays, examples of which can include bentonites, hectorites, and colloidal magnesium aluminum silicates. These and other suitable clays can be hydrophobically treated, and when so treated can generally be used in combination with a clay activator. Non-limiting examples of suitable clay activators can include propylene carbonate, ethanol, and combinations thereof. When clay activators are present, an amount of clay activator can typically range from about 40% or greater, about 25% or greater, about 15% or greater to about 75% or less, about 60% or less, or about 50% or less, by weight of the clay.

Additional non-limiting examples of suitable primary structurants can include hydrocarbon waxes such as paraffin wax; spermaceti wax; and polyethylenes with a molecular weight of about 200 to about 1000 Daltons. Other non-limiting examples of primary structurants suitable for use herein are described in U.S. Pat. No. 5,976,514 to Guskey et al. and U.S. Pat. No. 5,891,424 to Bretzler et al.

Solid stick antiperspirant compositions can further include a secondary structurant. In certain examples, the secondary structurant can be present in an amount from about 1% to about 10%, by weight of the solid stick antiperspirant composition. The secondary structurant can typically be included at an amount less than the primary structurant. Suitable secondary structurants can include any of those suitable as a primary structurant.

D. Other Ingredients

Solid stick antiperspirant compositions can further include perfumes. Perfumes can often be a combination of many raw materials, known as perfume raw materials. Any perfume suitable for use in a solid stick antiperspirant composition can be used herein.

A solid stick antiperspirant composition can further include any optional material that is known for use in antiperspirant and deodorant compositions or other personal care products, or which can otherwise be suitable for topical application to human skin.

One example of an optional ingredient can be a scent expression material. Scent expression or release technology can be employed with some or all of the fragrance materials to define a desired scent expression prior to use and during use of the solid stick antiperspirant compositions. Such scent expression or release technology can include cyclodextrin complexing material, like beta cyclodextrin. Other materials, such as, for example, starch-based matrices or microcapsules can be employed to "hold" fragrance materials prior to exposure to bodily-secretions (e.g., perspiration). The encapsulating material can have release mechanisms other than via a solvent; for example, the encapsulating material can be frangible, and as such, can rupture or fracture with applied shear and/or normal forces encountered during application and while wearing. A microcapsule can be made from many materials; one example can include polyacrylates.

Another example of optional materials can include clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue, which has been found to be a consumer negative for product acceptance. Therefore, it can be best to limit the solid stick antiperspirant composition to about 10% or less, about 8% or less, about 6% or less, or about 3% or less, by weight of the solid stick antiperspirant composition.

Non-limiting examples of other optional materials can include emulsifiers, distributing agents, antimicrobials, pharmaceutical or other topical active, preservatives, surfactants, and so forth. Examples of such optional materials are described in U.S. Pat. No. 4,049,792 to Elsnau; U.S. Pat. No. 5,019,375 to Tanner et al.; and U.S. Pat. No. 5,429,816 to Hofrichter et al.; descriptions of which are incorporated herein by reference.

In certain examples, a solid stick antiperspirant composition can be substantially or completely free of a modified starch particulate. In certain examples, the solid stick antiperspirant composition can be substantially or completely free of a polyamide powder.

Solid stick antiperspirant compositions can be applied to the skin by a user via an antiperspirant product. Such product can include a package having an interior chamber and the solid stick antiperspirant composition. A solid stick antiperspirant composition, as described herein, can be stored in the interior chamber and dispensed therefrom onto a desired surface of a consumer.

III. Product Characteristics

A solid stick antiperspirant composition can be defined in terms of an essential combination of ingredients as well as product characteristics, such as product hardness and other characteristics as described in U.S. Pat. No. 8,147,808 to Scavone et al. The term "product hardness" or "hardness" as used herein can reflect how much force can be required to move a penetration cone a specified distance and at a controlled rate into a solid stick antiperspirant composition under test conditions described herein below for the Penetration Test Method. Higher values represent harder product, and lower values represent softer product. For example, a solid stick antiperspirant composition can exhibit a product hardness of about 600 gram•force or greater, about 600 gram•force to about 5,000 gram•force, from about 750 gram•force to about 2,000 gram•force, or from about 800 gram•force to about 1,400 gram•force. Further, the solid stick antiperspirant composition can exhibit an average standard deviation of about 5 or less for penetration peak force measurements taken with a Penetration Test Method as described below.

In certain examples, the plurality of liquids, when mixed in the same proportions as in the solid stick antiperspirant composition, can have a light transmittance value of about 85% or greater after 4 hours at about −7° C. In certain examples, the plurality of liquids and the one or more waxes, when mixed in the same proportions as in the solid stick antiperspirant composition, can have a light transmittance value of about 85% or greater at about 85° C., at about 75° C., or at about 60° C. In certain examples, the plurality of liquids can form a homogeneous mixture at about −7° C. or at room temperature.

IV. Procedures

A. Cloud Point Test

Two hundred grams of a mixture of waxes plus a fixed amount of 5 cst dimethicone and an organic solvent are placed in a 400 mL beaker fitted with a magnetic stirring rod. The mixture is heated to 85° C. with constant stirring using IKA™ RET control-visc hot plate. Once the mixture reaches 85° C., it is stirred until homogeneous and/or a clear mixture is obtained. Then, stirring is increased to form a vortex, the cone of which reaches approximately the middle of the beaker. A thermometer probe is positioned so that the bottom of the probe stands about 1 inch from the bottom of beaker, and about two inches are submerged into the mixture. Then, the IKA™ temperature is set to 0° C. and the mixture is allowed to cool. The temperature when the mixture turns hazy (the cloud point) is noted.

B. Penetration Test Method

The Penetration Test Method can be run on samples that are conditioned at ambient conditions for 24 hours. Samples are prepared by advancing a solid antiperspirant to about ¼ inch above a rim of its container. This advanced portion can then be severed to expose a relatively clean, flat surface. A standard mechanical force analyzing instrument, such as a Texture Analyzer model TA-XT2i from Texture Technologies Corporation, can be used for penetration measurements. The instrument is equipped with a round, cylindrical probe measuring 0.040 inch in diameter. The probe extends approximately 1 inch below where it attaches to the instrument. A product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, an angled cone length of about 18.3 mm, and a maximum diameter of the angled surface of the cone of about 15.5 mm. The cone can have a smooth, stainless steel construction and weighs about 17.8 grams.

For each sample run, the probe is advanced into a prepared surface of a sample at a rate of 5 mm/sec for 2 seconds (total penetration of 1 cm). The resistant force is measured at a rate of 200 data points per second. Multiple readings (e.g., at least 8) are taken for each sample. Each reading can be about 3 mm or less from an adjacent wall of a sample container, about 3 mm or less from a center screw hole (or axis), and about 5 mm or less from another reading site. A typical pattern P1 is shown in FIG. 1, with reading sites 51-58. Various metrics are recorded using the Penetration Test Method, including maximum peak force and Hardness Modulus, which can be calculated as the maximum slope (force/time) between any four consecutive data points gathered during a first 0.5 sec of a test run in a linear visco-elastic region. Standard deviations of the peak force and Hardness Modulus can be calculated across multiple reading sites (e.g., across the 8 sites shown in FIG. 1). Five samples can be tested and average standard deviations can be used to compare products.

V. Examples

A. Inventive Example 1

Table 8 shows the formulation for Inventive Example 1.

TABLE 8

| Inventive Example 1 | |
|---|---|
| Ingredient | Amount (wt. %) |
| Polydimethylsiloxane (5 cst) | 32.55 |
| Stearyl Alcohol | 15.00 |
| Aluminum Chlorohydrate (86% Active) | 14.00 |
| Talc USP | 8.00 |
| Isopropyl Myristate | 8.00 |
| C12-15 Alkyl Benzoate | 5.00 |
| Hydrogenated Castor Oil | 4.00 |
| Petrolatum | 3.00 |
| Cyclodextrin | 3.00 |
| Mineral Oil | 3.00 |
| PPG-14 Butyl Ether | 3.00 |
| Perfume | 0.75 |
| PEG-12 Dimethicone | 0.50 |
| Behenyl Alcohol | 0.20 |

Inventive Example 1 was prepared by first mixing the liquids in a vessel. After mixing heating the mixture to about 85° C., the waxes can be added until dissolved into the liquids. Then, powders can be added to the mixture. The mixture can then be cooled to about 55° C. to about 60° C. and poured into a container or package. Inventive Examples 2-6, as shown below in Table 9, were prepared in a similar manner. As illustrated in Table 9, each of the compositions for Inventive Examples 2-6 had an aggregate polarity in a desired range.

TABLE 9

| | Amount (wt. %) | | | | |
|---|---|---|---|---|---|
| Ingredient | Inventive Ex. 2 | Inventive Ex. 3 | Inventive Ex. 4 | Inventive Ex. 5 | Inventive Ex. 6 |
| Poldimethylsiloxane (5 cst) | 26.38 | 32.55 | 30.00 | 37.70 | 31.70 |

TABLE 9-continued

| Ingredient | Amount (wt. %) | | | | |
|---|---|---|---|---|---|
| | Inventive Ex. 2 | Inventive Ex. 3 | Inventive Ex. 4 | Inventive Ex. 5 | Inventive Ex. 6 |
| PPG-14 Butyl Ether | 3.00 | 3.00 | 4.30 | 1.00 | 3.00 |
| Isopropyl Myristate | 8.00 | 8.00 | 14.00 | 8.00 | — |
| C12-15 Alkyl Benzoate | 5.00 | 5.00 | — | — | — |
| Mineral Oil | 1.00 | 3.00 | 1.00 | 1.00 | 12.00 |
| Talc USP | 5.00 | 8.00 | 7.00 | 3.00 | 3.00 |
| BCDs | 3.00 | 3.00 | 3.00 | 3.00 | 3.00 |
| PEG-12 dimethicone | — | 0.50 | — | 0.50 | 0.50 |
| Performathox 450 Ethoxylate | 2.00 | — | 2.00 | — | — |
| Stearyl Alcohol | 12.00 | 15.00 | 16.00 | 14.00 | 15.00 |
| Hydrogenated Castor Oil | 4.00 | 4.00 | 4.75 | 3.85 | 3.85 |
| Behenyl Alcohol | 0.20 | 0.20 | 0.20 | 0.20 | 0.20 |
| Petrolatum | 3.00 | 3.00 | 3.00 | 3.00 | 3.00 |
| Aluminum Chlorohydrate | — | 14.00 | 14.00 | — | — |
| AZAG | 26.67 | — | — | 24.00 | 24.00 |
| Fragrance | 0.75 | 0.75 | 0.75 | 0.75 | 0.75 |
| Aggregate Polarity $MPa^{1/2}$ | 2.5 | 2.3 | 2.7 | 1.8 | 1.7 |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The products and methods/processes of the present disclosure can comprise, consist of, and consist essentially of the essential elements and limitations of the invention described herein, as well as any of the additional or optional ingredients, components, steps, or limitations described herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A solid stick antiperspirant composition comprising:
   a. an particulate antiperspirant active;
   b. one or more waxes comprising a polar wax; and
   c. from about 30% to about 70% of a plurality of liquids comprising a first emollient and a second emollient, wherein the first emollient is polydimethylsiloxane, the polydimethylsiloxane having a viscosity of about 2 to about 6 centistokes and being present at about 60% or greater, by weight, of the plurality of liquids and the second emollient is present at about 16% to about 40%, by weight, of the plurality of liquids, and wherein the plurality of liquids are a homogeneous mixture at room temperature and have a an aggregate polarity from 0.9 $MPa^{1/2}$ to 3.4 $MPa^{1/2}$; and wherein the plurality of liquids, when mixed, have a light transmittance of 85% or greater after 4 hours at −7° C.;
   wherein the solid stick antiperspirant composition is free of volatile silicones;
   wherein the solid stick comprises 2% or less water; and
   wherein the one or more waxes and the plurality of liquids, when mixed, exhibit a cloud point temperature between about 45° C. and about 65° C.

2. The solid stick antiperspirant composition of claim 1, wherein the polydimethylsiloxane has the following formula:

wherein M is $(CH_3)_3SiO$, D is $((CH_3)_2SiO)$, and x is from 4 to 11.

3. The solid stick antiperspirant composition of claim 1, wherein the polydimethylsiloxane is from about 25% to about 50%, by weight of the solid stick antiperspirant composition.

4. The solid stick antiperspirant composition of claim 1, wherein the second emollient has a concentration of about 20% or less, by weight of the solid stick antiperspirant composition.

5. The solid stick antiperspirant composition of claim 1, wherein the second emollient has a concentration of about 15% or less, by weight of the solid stick antiperspirant composition.

6. The solid stick antiperspirant composition of claim 1, wherein the polar wax has a concentration from about 10% to about 20%, by weight of the solid stick antiperspirant composition.

7. The solid stick antiperspirant composition of claim 1, wherein the polar wax comprises a fatty alcohol wax having a carbon chain length from 12 to 40.

8. The solid stick antiperspirant composition of claim 1, wherein the polar wax has a carbon chain length from 14 to 24.

9. The solid stick antiperspirant composition of claim 1, wherein the polar wax comprises a fatty alcohol wax selected from the group consisting of stearyl alcohol, behenyl alcohol, cetyl alcohol, ceryl alcohol, and ceteryl alcohol.

10. The solid stick antiperspirant composition of claim 1, wherein the one or more waxes further comprise hydrogenated castor oil or solid triglycerides.

11. The solid stick antiperspirant composition of claim 1, wherein the one or more waxes have a concentration from about 5% to about 35%, by weight of the solid stick antiperspirant composition.

12. The solid stick antiperspirant composition of claim 1, wherein the one or more waxes have a concentration from about 15% to about 25%, by weight of the solid stick antiperspirant composition.

13. The solid stick antiperspirant composition of claim 1 having a total particulate concentration of about 30% or less, by weight.

14. The solid stick antiperspirant composition of claim 1 being substantially or completely free of a modified starch particulate.

15. The solid stick antiperspirant composition of claim 1 exhibiting an average standard deviation of about 5 or less for penetration peak force measurements taken in accordance with the Penetration Test Method as described herein.

16. The solid antiperspirant composition of claim 1, wherein the plurality of liquids comprise from about 60% to about 75%, by weight of the plurality of liquids, of the polydimethylsiloxane.

\* \* \* \* \*